United States Patent [19]

Smathers

[11] 4,101,577

[45] Jul. 18, 1978

[54] PROCESS FOR MAKING LOWER ALKYL FORMAMIDES

[75] Inventor: Donald Lee Smathers, Wilmington, Del.

[73] Assignee: E. I. Du Pont de Nemours and Company, Wilmington, Del.

[21] Appl. No.: 772,860

[22] Filed: Feb. 28, 1977

[51] Int. Cl.² ............................................. C07C 97/16
[52] U.S. Cl. ............................ 260/561 R; 260/562 R
[58] Field of Search ....................... 260/561 R, 562 R

[56] References Cited

U.S. PATENT DOCUMENTS

| | | | |
|---|---|---|---|
| 3,274,243 | 9/1966 | Gilbert et al. | 260/551 S |
| 3,336,381 | 8/1967 | Gilbert et al. | 260/551 S |
| 3,346,632 | 10/1967 | Tull et al. | 260/551 S |
| 3,979,452 | 9/1976 | Axelrod | 260/551 S |

*Primary Examiner*—Paul F. Shaver

[57] ABSTRACT

A process for making formamides by contacting an intimate admixture of (a) gaseous CO, (b) a non-tertiary amine and (c) a lower alkanol with a strongly basic anion exchange resin.

16 Claims, No Drawings

PROCESS FOR MAKING LOWER ALKYL FORMAMIDES

FIELD OF THE INVENTION

The invention relates to an improved process for making formamides by the catalytic reaction of non-tertiary amines with CO. In particular, the invention relates to the use of an heterogeneous catalyst for the process.

BACKGROUND OF THE INVENTION

Substituted formamides are clear colorless liquids or solids which are miscible both with water and/or common organic solvents. As a result of these properties, they find extensive use in industry. The more widely used substituted formamides are the lower alkyl formamides of which dimethylformamide is the most widely used of all. Dimethylformamide (DMF) finds extensive use as a solvent for vinyl resins in lacquers, films and printing inks, for polyurethanes, polyacrylics, pigments, dyes and organic reactions such as halogenation, alkylation, elimination, cyclization and many others. It also finds use as a reaction medium in dyes and as a selective refining solvent for acetylene, acid gases and petroleum constituents.

Virtually all substituted formamides are made by a process involving the reaction of a non-tertiary amine with methyl formate or with gaseous carbon monoxide (CO) in the presence of a catalyst.

DISCUSSION OF THE PRIOR ART

Heretofore, most processes for making substituted amides have been carried out using an homogeneous catalyst. For example, Giachino in U.S. Pat. No. 2,677,706 discloses the reaction in either the liquid or vapor phase of methylamines with CO at high temperature (50°–300° C) and high pressure (1000–15,000 psia) using a dissolved catalyst such as $CuCl_2$ and potassium acetate. Similarly, Lo Cicero et al in U.S. Pat. No. 2,793,211 disclose the reaction of non-tertiary amines with CO at above 500 psia in the presence of a catalyst such as choline (oxyethyltrimethylammonium hydroxide) dissolved in methanol. On the other hand, Siefen et al in U.S. Pat. No. 2,866,822 disclose the reaction of methylamines with CO at more moderate conditions of temperature and pressure (60°–130° C, 90–130 psia) using as catalyst alkali metal dissolved in methanol. Similarly to the above-mentioned Siefen patent, U.K. Pat. No. 1,213,173 assigned to Nitto Chemical Industry discloses the sparging of CO gas through liquid dialkylamine to form the corresponding formamide. The disclosed catalyst is a solution of sodium methylate in methanol. Somewhat related processes are also disclosed by the prior art in which $H_2$ and CO are reacted with amines to produce substituted formamides. For example, in U.S. Pat. No. 3,530,182, Haynes et al disclose that alkyl formamides are prepared by reacting $CO_2$, $H_2$ and aliphatic amines in the presence of a soluble transition metal halide catalyst such as copper chloride. In a similar fashion, U.K. Pat. No. 690,131 discloses the preparation of N-mono- and N,N'-dialkylformamides by treating primary or secondary amines at high temperature and pressure with CO and $H_2$ in the presence of alkali metal alcoholate catalyst.

In addition to the foregoing processes in which formamides are made directly from CO and dialkylamines, various commercial processes utilize the reaction of methyl formate and dimethylamine to produce dimethylformamide. However, the methyl formate for this process is produced by reaction of CO and methanol in the presence of a sodium methylate catalyst.

As can be seen from the foregoing description of the prior art, substituted formamides have heretofore been made using a homogeneous catalyst system, which frequently was quite difficult to remove from the reaction mixture and added greatly to both the capital and operating costs of the commercial processes. For example, when using the well-known sodium methylate catalyst system, it is necessary to dilute the product with water whereupon product DMF is hydrolyzed to sodium formate and dimethylamine (DMA). Then the sodium formate must be filtered out and the DMA stripped from the filtrate. Such procedure is, of course, costly from the standpoints of reduced yield and energy consumption, as well as high capital costs for the equipment to carry out the separation steps.

BRIEF SUMMARY OF THE INVENTION

It has now been discovered that formamides can be made by a process which comprises the steps of contacting an intimate admixture of (a) gaseous CO, (b) a non-tertiary amine and (c) a lower alkanol with a strongly basic anion exchange resin. In particular, the process is carried out at temperatures of 0°–200° C at a CO partial pressure of 100–5,000 psia.

DETAILED DESCRIPTION OF THE INVENTION

The reaction on which the processes of the prior art as well as the invention are based is as follows:

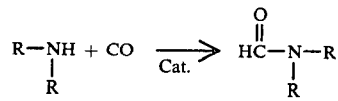

Suitable non-tertiary amines include ammonia and both primary and secondary amines which are mutually soluble with lower alkanols and in which the R groups are independently selected from the group consisting of hydrogen, alkyl, alkenyl, aralkyl, aminoalkyl and alkanol groups having 1–10 carbon atoms. In addition, the R groups taken together may be a divalent moiety which together with the imine nitrogen (=NH) forms a cyclic secondary amine such as piperidine or pyrrolidine. In view of more rapid reaction rates and greater solvency, it is preferred that the R groups contain 1–4 carbon atoms. Furthermore, when the R groups together constitute a divalent moiety as described above, it is preferred that the resultant moiety be comprised of a 4 or 5 member carbon chain. Suitable non-tertiary amine reactants for the process of the invention include ammonia and the following:

Primary Amines a. Alkyl amines
methylamine
ethylamine
butylamine
hexylamine
cyclohexylamine
decylamine
b. Alkenyl amines
allylamine
butenylamine cycloheptenylamine
c. Aralkyl amines
benzylamine
phenylbutylamine
d. Alkyldiamines
ethylenediamine
hexamethylenediamine
1,4-diamino-2-methylbutane
e. Alkanol amines
ethanolamine
propanolamine
heptanolamine
decanolamine

Secondary Amines a. Dialkylamines
dimethylamine
methylethylamine
diethylamine
ethylhexylamine
b. Diaralkylamines
dibenzylamine
di(propylbenzyl) amine
c. Aralkylalkanolamines
benzylaminomethanol
naphthylaminomethanol
d. Dialkyldiamines
N,N'-dimethylethylenediamine
N,N'-diethylhexamethylenediamine
e. Alkylalkanolamines
methylaminoethanol
ethylaminoethanol
f. Heterocyclic amines
pyrrolidone
morpholine
piperidine By far the most important of the many useful non-tertiary amines which can be used in the process is dimethylamine.

It has been found that at least a small amount of lower alkanol must be present for the reaction to take place with any useful degree of conversion. Suitable lower alkanols are the $C_{1-4}$ alkanols of which methanol is preferred because of its higher volatility and consequent ease of separation from the reaction mixture. At least about 0.01% wt. lower alkanol should be used, and it is preferred to use 2-7% wt. alkanol, basis total liquid feed to the reaction zone. From 5 to 50% wt. alkanol is most preferred. In general, higher amounts of alkanol will be preferred when amine solubility in the system is low. However, the upper limit is not at all critical and will ordinarily be governed by practical considerations such as its effect upon the amount of energy needed for purification and equipment sizes. The alkanol is readily removed from the reaction mixture by distillation and can be recycled to the process.

The carbon monoxide for the reaction need not be of especially high purity. Consequently either rather pure CO or quite dilute CO mixtures such as a synthesis gas can be used in the process since most diluents such as $N_2$ and $H_2$ will go through the process unchanged. The purity of CO feed is therefore likewise a matter of economics. Obviously, the presence of diluent increases the gas handling and equipment size requirements and will be preferably minimized in most instances. It is preferred that the CO feed to the process be substantially free of $CO_2$ since its presence will reduce catalyst effectiveness. Various pretreatments can, of course, remove the $CO_2$ from CO-containing gas streams having excessive amounts of $CO_2$.

It will ordinarily be preferred to use approximately stoichiometric ratios of CO and amine since the amount of unreacted feed materials is minimized thereby. Nevertheless, the mole ratio of reactants is not at all critical and can range from as low as 0.05 to as high as 20 CO/amine. It is preferred, however, to operate at a feed mole ratio of CO to amine which is from 0.1 to 3.0 and preferably still about 0.5 to 1.5.

In order to obtain better mass transfer and generally more rapid reaction rates, it is preferred to operate the process at CO partial pressure of at least 100 psi. Moreover, useful operating pressures extend to at least about 5000 psia or even higher. However, economically preferred operating pressures are 100-1500 psia CO partial pressure and especially 1000-1500 psia.

The heterogeneous catalyst used in the process of the invention must be a strongly basic anion exchange resin. Typical of such resins is poly(styrene-divinylbenzene), the ion-active portion of which is a quaternary ammonium group. These materials are prepared by chloromethylation of the solid copolymer, usually in bead form, using chloromethyl methyl ether and a Friedel-Crafts catalyst such as aluminum chloride, stannic chloride, ferric chloride or zinc chloride:

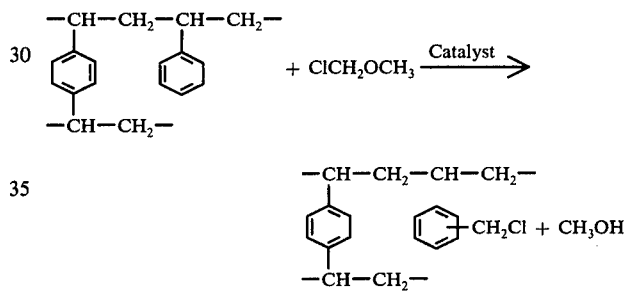

The chloromethylated resin is then reacted with a tertiary amine dissolved in polar solvent to form a quaternary ammonium salt

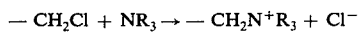

An alternative approach is by side chain chlorination of poly(vinyl toluene) to form poly(vinyl benzyl chloride) which is then treated with tertiary amine to form the quaternary ammonium salt.

A variety of tertiary amines can be used to form the ion-active group for the polymer matrix especially those corresponding to the structure $NR_3$ in which the R groups are .ndependently selected from the group consisting of $C_{1-4}$ alkyl and hydroxyl-substituted $C_{1-2}$ alkyl groups. However, those which are most widely available are derived from trimethylamine and dimethylethanolamine. Commercially available resins prepared from trimethylamine include Amberlite[1] IRA-400, Amberlite IRA-401, Amberlite IRA-402, Amberlite IRA-900, Amberlite 900C, Amberlite 938, Duolite[2] A-101-D, Duolite ES-111, Dowex[3] 11, Dowex 21K and Ionac[4] A-540. Commercially available resins prepared from dimethylethanolamine include Amberlite IRA-410, Amberlite IRA-911, Dowex 2, Duolite A-102-D, Ionac A-542 and Ionac A-550. Other available quaternary ammonium resins include Amberlyst[1] A-26 and Amberlyst A-27.

[1]Trade name of Rohm & Haas Co., Philadelphia, PA

[2] Trade name of Diamond Alkali Co., Redwood City, CA
[3] Trade name of The Dow Chemical Co., Midland, MI
[4] Trade name of Ionac Chemical Co., Div. of Plaudler Permutit Inc., Birmingham, NJ The above-described ion-exchange resins are available in particulate form as granules or spheres usually ranging from about 400 mesh (about 40M) to 16 mesh (1.2 mm) and have a specific gravity in the range of 1.1–1.5. These materials can be used in the process of the invention either as a fixed foraminous bed through which the reactants are passed either upwardly or downwardly or the resin can be slurried in the reactants and then separated from the reaction mixture by settling and/or filtration. A continuously moving bed of catalyst may also be used, especially when the resin catalyst has suitable resistance to attrition.

Because the catalyst is completely insoluble in the reactants and product and is in particulate form, the process can be carried out either batchwise or continuously. When the process is carried out batchwise, the resin catalyst is slurried in the reactants for a time sufficient to assure contact with the resin surface, separated from the reaction mixture by settling and decantation or by filtration of the slurry. It is preferred, however, to carry out the process continuously by passing the reactants through a fixed bed of resin. A preferred manner of doing this is to pass a downflowing stream of the solution of alkanol and amine reactant through a fixed bed of catalyst resin while simultaneously passing downwardly through the bed a finely divided stream of gaseous CO. Any unconverted CO and/or diluent is then passed from the bottom of the contacting vessel for purification, recycle or other disposition and liquid formamide product dissolved in the alkanol and/or unreacted amine is also withdrawn from the contacting vessel. Countercurrent operation of the reactor is also quite feasible. Because the boiling points of lower alkanol and the non-tertiary amine are normally different than the boiling point of the formamide produced therefrom, the alkanol and unreacted amine are readily removed from the reaction mixture by distillation in most instances.

The process of the invention can be carried out at a temperature of as low as 0° C or even lower and in theory could be carried out at quite high temperatures as well. However, as a practical matter, the reaction should be carried out below the temperature at which the life of the resin catalyst becomes unacceptable. A suitable range of temperature is 0°–200° C, 20°–100° C being preferred.

The overall reaction between CO and amines to form formamides is quite exothermic. This, of course, means that a considerable amount of heat must be removed from the system to avoid overheating the catalyst. One preferred way of doing this is to recycle cold reaction product to the reactor to absorb heat of reaction. The formamide component of the reaction product is inert and thus functions as a heat sink to keep the temperature of the reactants and the catalyst at a suitably low level. The warm reaction product can then be cooled by conventional external heat exchangers. It is preferred to recycle 5–98% and still more preferably 30–95% by weight of the reaction mixture for this purpose.

The time of contact of the reactants and catalyst required to effect the conversion depends upon a number of operating variables such as conversion level, temperature, pressure, formamide type, production rates and the like. It is, however, necessary that the velocity of each phase through the foramina of the catalyst bed be such as to assure a residence time of at least 0.1 second and preferably 1 second within the catalyst bed. Higher conversion of amine to formamide is favored by longer contact times with the resin catalyst and therefore residence times as long as 20–30 minutes can be used to attain extremely high single-pass conversions.

EXAMPLE I

This example illustrates the method of resin preparation which was used for the process examples which follow.

Fifty ml of A-26 macroreticular ion exchange resin in the chloride form were charged to a 100 ml buret in the form of an aqueous slurry. The resin was converted to the hydroxyl form with 1N NaOH by slowly introducing 250 ml of the caustic solution into the top of the buret while simultaneously withdrawing an equal volume of liquid from the tip. Following this caustic wash, the resin was washed with water to remove excess caustic. In addition, to reduce the incidence of hydrolysis of formamide reaction product, the water in the buret surrounding the resin was displaced by a like amount of the lower alkanol to be used in subsequent test runs to make formamides.

EXAMPLE II

Two ml of the resin from Example I, one ml of methanol and one gram of dimethylamine were charged to a 10 ml shaker tube. A source of pressurized CO was connected to the tube and the pressure of CO adjusted to 1,000 psia. The temperature within the shaker tube was maintained at 50° ± 3° C by an external heat exchanger and controller. After 24 hours, the shaker was cooled and depressurized. The yield of DMF was essentially quantitative.

EXAMPLE III

Other similar quaternary ammonium ion exchange resins converted to the hydroxyl form by the procedure of Example I are found to be similarly useful for the preparation of a wide variety of formamide products. Likewise, lower alkanols other than methanol are found to be useful solvents for carrying out reactions between CO and non-tertiary amines in the presence of the above-described highly basic ion exchange resins.

Using essentially the same reaction conditions as in Example II, the following products are obtained from the below-listed reactants:

TABLE 1

| Resin | Lower Alkanol Solvent | Non-tertiary Amine | Formamide Product |
|---|---|---|---|
| IRA-938 | Methanol | Pyrrolidine | N-Formylpyrrolidine |
| " | Ethanol | Piperidine | N-Formylpiperidine |
| IRA-900C | Methanol | N,N'-Dimethylethylenediamine | N,N'-Dimethyl-N,N'-Diformyl ethylenediamine |
| " | Propanol | Cyclohexylamine | N-Cyclohexylformamide |
| IRA-900 | Methanol | Benzylamine | N-Benzylformamide |
| " | 2-Propanol | Ethanolamine | N-(2-hydroxyethyl)formamide |
| A-26 | Methanol | Ethylenediamine | N,N'-Diformylethylenediamine |

TABLE 1-continued

| Resin | Lower Alkanol Solvent | Non-tertiary Amine | Formamide Product |
|---|---|---|---|
| " | Ethanol | sec-Butylamine | N-sec-Butylformamide |
| " | n-Butanol | N-Butylamine | N-n-butylformamide |
| " | Methanol | Allylamine | N-Allylformamide |
| " | i-Butanol | Propylamine | N-Propylformamide |
| " | Methanol | Diethylamine | N,N'-diethylformamide |
| " | sec-Butanol | Ethylamine | N-Ethylformamide |
| " | Methanol | Methylamine | N-Methylformamide |

EXAMPLE IV

The efficacy of the resin as catalyst for the reaction between non-tertiary amines and CO to form formamides is shown by the following tests. In the first of two tests, a mixture of 150 ml of resin catalyst from Example I, 120 g of methanol and 41 g of dimethylamine is held at 50° C for 18 hours in contact with CO at 1000 psia. Fractionation of the product yields 65 g of dimethylformamide (98% yield). When the same procedure is repeated without the resin catalyst, no detectable amount of dimethylformamide is produced.

EXAMPLE V

A stirred reactor is charged with 450 g dimethylformamide (DMF), 150 ml resin catalyst prepared as in Example I, 100 g methanol and 45 g dimethylamine. After sealing the reactor, CO gas is introduced gradually to the reactor while maintaining the temperature of the reactants at 15° C until the reaction pressure reaches 3,000 psia at which it is maintained throughout. After 36 hours, the amount of unreacted dimethylamine is determined by titration and it is found that a substantial amount of the dimethylamine has been converted even at this comparatively low reaction temperature.

EXAMPLE VI

In this example, the effect of higher pressure in improving conversion to formamide can be seen.

A 0.5 inch O.D. stainless steel tubular reactor was charged with 40 ml of A-26 ion exchange resin prepared in the manner described in Example I. The reactor was then charged with a liquid solution consisting of 1% wt dimethylamine and 99% wt methanol while simultaneously pressurizing the reactor with CO gas to 100 psig. Maintaining the reaction system at 34° C and at the same CO pressure, a liquid reactant flow rate of 0.17 g/sec and CO flow rate of 1 cm$^3$/sec was established through the reactor. Analysis of the effluent liquid revealed that conversion of dimethylamine exceeded 2% by weight. When the same procedure was repeated at 1000 psig, the conversion of dimethylamine increased to above 10% by weight.

I claim:

1. A process for making formamides comprising contacting and reacting an intimate admixture of (a) gaseous CO, and (b) a nontertiary amine in the presence of a $C_{1-4}$ alkanol and a strongly basic anion exchange resin by which a reaction mixture is formed containing a formamide.

2. The process of claim 1 in which the non-tertiary amine corresponds to the formula

wherein the R groups are independently selected from the group consisting of hydrogen, alkyl, alkenyl, aralkyl, aminoalkyl and alkanol groups having 1-10 carbon atoms, and the R groups taken together with the imine nitrogen form a 5- or 6-membered heterocyclic secondary amine.

3. The process of claim 2 in which the non-tertiary amine is dimethylamine.

4. The process of claim 1 in which the alkanol is methanol.

5. The process of claim 1 in which the polymer matrix of the anion exchange resin is poly(styrenedivinylbenzene).

6. The process of claim 1 in which the ionactive group of the anion exchange resin corresponds to the structural formula —$CH_2NR_3^+$ in which the R groups are independently selected from the group consisting of $C_{1-4}$ alkyl and hydroxyl-substituted $C_{1-2}$ alkyl groups.

7. The process of claim 6 in which the ion-active group is derived from trimethylamine.

8. The process of claim 6 in which the ion-active group is derived from dimethylethanolamine.

9. The process of claim 1 in which the contacting step is carried out at 0°–200° C.

10. The process of claim 1 in which the contacting step is carried out at 100–5,000 psia.

11. The process of claim 1 in which the process is carried out continuously in a closed reactor having a fixed foraminous bed of resin catalyst.

12. The process of claim 10 in which the contacting step is carried out by passing the solution of non-tertiary amine and alkanol and the CO concurrently through the catalyst bed.

13. The process of claim 10 in which 5–98% by weight of the reaction mixture is cooled before separation of the formamide and recycled to the reactor.

14. The process of claim 12 in which the portion of the reaction mixture to be recycled is blended with non-tertiary amine reactant and alkanol and then recycled to the reactor.

15. The process of claim 10 in which the contacting step is carried out countercurrently through the catalyst bed.

16. The process of claim 1 in which the alkanol constitutes 2–70% by weight of the liquid feed to the reaction zone.

* * * * *